US010898059B2

(12) United States Patent
Yamagata (10) Patent No.: US 10,898,059 B2
(45) Date of Patent: Jan. 26, 2021

(54) ENDOSCOPE BENDING TUBE MANUFACTURING METHOD

(71) Applicant: OLYMPUS CORPORATION, Hachioji (JP)

(72) Inventor: Kazuhiro Yamagata, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 14 days.

(21) Appl. No.: 16/165,825

(22) Filed: Oct. 19, 2018

(65) Prior Publication Data

US 2019/0053688 A1 Feb. 21, 2019

Related U.S. Application Data (63) Continuation of application No. PCT/JP2017/017916, filed on May 11, 2017.

(30) Foreign Application Priority Data

May 18, 2016 (JP) .................................. 2016-099800

(51) Int. Cl.
*A61B 1/00* (2006.01)
*A61B 1/008* (2006.01)
(Continued)

(52) U.S. Cl.
CPC ............ *A61B 1/0011* (2013.01); *A61B 1/008* (2013.01); *A61B 1/0055* (2013.01); *G02B 23/24* (2013.01)

(58) Field of Classification Search
CPC ..... A61B 1/0011; A61B 1/0055; A61B 1/008; G02B 23/24
See application file for complete search history.

(56) References Cited

U.S. PATENT DOCUMENTS 4,108,211 A * 8/1978 Tanaka ................. A61B 1/0055
138/120
4,834,069 A * 5/1989 Umeda ................. A61B 1/0055
138/120
(Continued)

FOREIGN PATENT DOCUMENTS

JP S61249428 A 11/1986
JP S6238132 A 2/1987
(Continued)

OTHER PUBLICATIONS

Japanese Office Action dated Apr. 7, 2020 (and English translation thereof) issued in Japanese Application No. 2016-099800.
(Continued)

*Primary Examiner* — Lawrence Averick
(74) *Attorney, Agent, or Firm* — Holtz, Holtz & Volek PC (57) ABSTRACT

An endoscope bending tube manufacturing method includes: arranging one of two adjacent ring tubes on an outer side of an other one of the two adjacent ring tubes; after inserting a connecting shaft through both a through hole of an outer ring tube and a through hole of an inner ring tube, performing processing of making an end portion of the connecting shaft increase in diameter by plastic working of pushing and stretching the end portion in a radial direction of the connecting shaft; fixing an outer peripheral surface of the connecting shaft to the through hole of the outer ring tube by bringing the outer peripheral surface into close contact with the through hole of the outer ring tube; and rotatably connecting the one of the two adjacent ring tubes to the other one of the two adjacent ring tubes.

2 Claims, 5 Drawing Sheets

(51) Int. Cl.
    *G02B 23/24*     (2006.01)
    *A61B 1/005*     (2006.01)

(56) References Cited

U.S. PATENT DOCUMENTS

| | | | | |
|---|---|---|---|---|
| 5,178,129 | A * | 1/1993 | Chikama | A61B 1/0051 138/120 |
| 6,408,889 | B1 * | 6/2002 | Komachi | A61B 1/0055 138/120 |
| 8,182,418 | B2 * | 5/2012 | Durant | A61B 1/0055 600/141 |
| 8,568,299 | B2 * | 10/2013 | Eno | A61B 1/00039 600/117 |
| 9,192,288 | B2 * | 11/2015 | Okaniwa | A61B 1/0055 |
| 9,357,901 | B2 * | 6/2016 | Eno | A61B 1/0057 |
| 10,426,412 | B2 * | 10/2019 | Eno | A61B 1/00039 |
| 10,512,392 | B2 * | 12/2019 | Gurusamy | A61B 1/0053 |
| 2002/0032371 | A1 | 3/2002 | Torii | |
| 2007/0270650 | A1 * | 11/2007 | Eno | A61B 1/00039 600/145 |
| 2009/0216083 | A1 * | 8/2009 | Durant | A61B 1/0055 600/130 |
| 2011/0295065 | A1 * | 12/2011 | Gurusamy | A61B 1/008 600/114 |
| 2013/0041224 | A1 * | 2/2013 | Okaniwa | A61B 1/0056 600/142 |
| 2014/0094648 | A1 * | 4/2014 | Eno | A61B 1/0057 600/103 |
| 2016/0331331 | A1 * | 11/2016 | Eno | A61B 1/0055 |

FOREIGN PATENT DOCUMENTS

| | | |
|---|---|---|
| JP | 2002078674 A | 3/2002 |
| JP | 2002159442 A | 6/2002 |
| JP | 2008188095 A | 8/2008 |
| JP | 2016000128 A | 1/2016 |

OTHER PUBLICATIONS

Japanese Office Action (and English language translation thereof) dated Dec. 17, 2019 issued in counterpart Japanese Application No. 2016-099800.
International Search Report (ISR) dated Jul. 4, 2017 issued in International Application No. PCT/JP2017/017916.
Written Opinion dated Jul. 4, 2017 issued in International Application No. PCT/JP2017/017916.

* cited by examiner

ENDOSCOPE BENDING TUBE MANUFACTURING METHOD

CROSS-REFERENCE TO RELATED APPLICATION

This application is a continuation of PCT International Application No. PCT/JP2017/017916 filed on May 11, 2017 which claims the benefit of priority from Japanese Patent Application No. 2016-099800, filed on May 18, 2016, the entire contents of which are incorporated herein by reference.

BACKGROUND

1. Technical Field

The present disclosure relates to an endoscope bending tube manufacturing method.

2. Related Art

Figure 7:
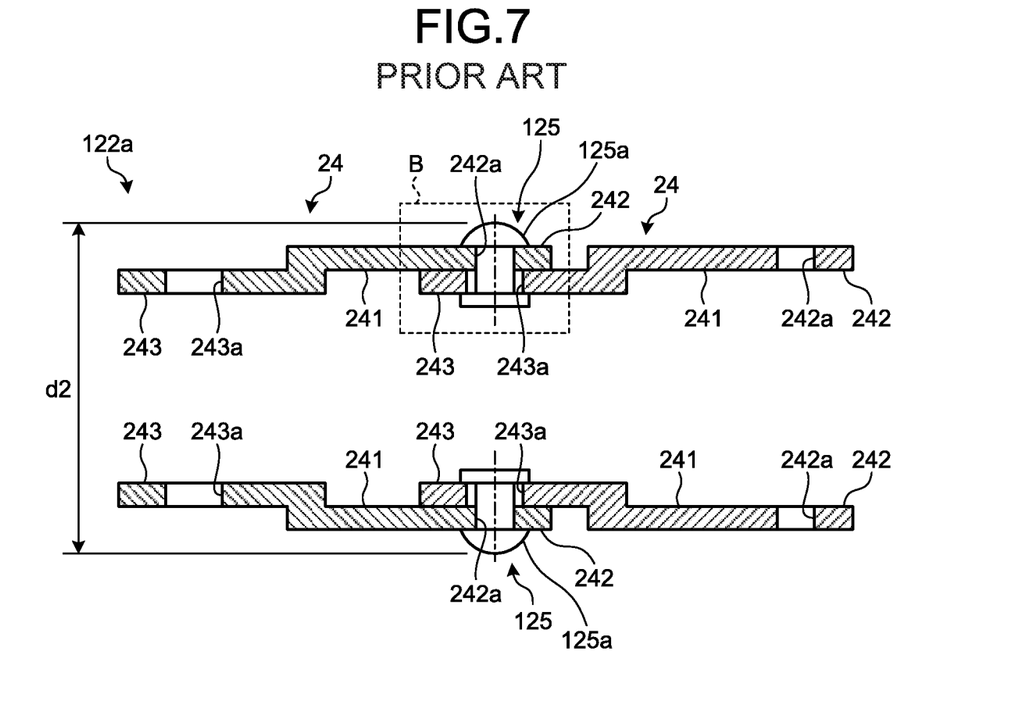
FIG. 7 is a sectional view illustrating a configuration of an endoscope bending tube according to a conventional technique.

In related art, manufacturing methods for endoscope bending tubes include a method where plural ring tubes are connected in series. For example, in Japanese Laid-open Patent Publication No. 2008-188095, as illustrated in FIG. 7, each ring tube 24 has tongue pieces 242 and 243 respectively provided at one end and the other end thereof, the tongue pieces 242 and 243 having through holes 242a and 243a formed therein. Adjacent ones of the ring tubes 24 are connected by: insertion of a connecting shaft 125 through the through holes 242a and 243a of these adjacent ring tubes 24, the through holes 242a and 243a having been overlapped with each other; and formation of a retaining portion 125a for the through holes 242a and 243a by caulking of an end portion of the connecting shaft 125.

Figure 8:
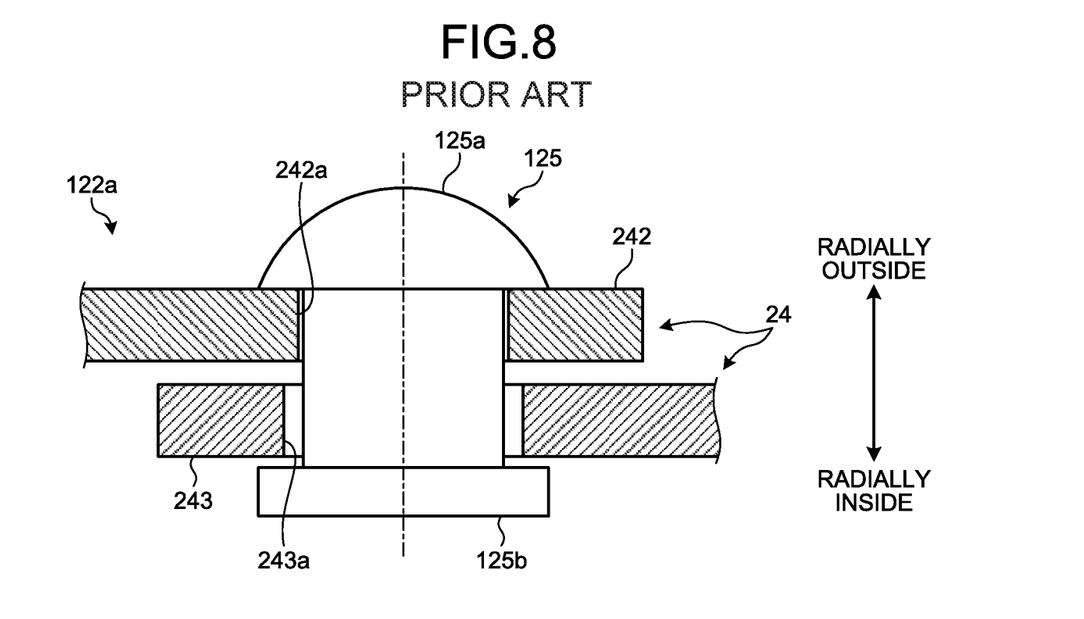
FIG. 8 is a sectional view illustrating the configuration of the endoscope bending tube according to the conventional technique, the sectional view being an enlarged view of a B-portion in FIG. 7.

However, in this method disclosed in Japanese Laid-open Patent Publication No. 2008-188095, as illustrated in FIG. 8, since the retaining portion 125a of the connecting shaft 125 formed by the caulking protrudes radially outward from a bending tube 122a, an outer diameter d2 of the bending tube 122a is increased by an amount of that protrusion. Further, since a head portion 125b protrudes radially inward from the bending tube 122a at a side opposite to the retaining portion 125a, if the inner diameter is decreased, the head portion 125b interferes with a built-in element housed in the bending tube 122a. Such protrusion has hindered reduction in the diameter of the bending tube.

SUMMARY

In some embodiments, provided is an endoscope bending tube manufacturing method of manufacturing a bending tube of an endoscope, by connecting plural ring tubes forming the bending tube. The endoscope bending tube manufacturing method includes: arranging one of two adjacent ring tubes on an outer side of an other one of the two adjacent ring tubes to match positions of a pair of through holes formed at one end of the one that is an outer ring tube, with positions of a pair of through holes formed at one end of the other one that is an inner ring tube; after inserting a connecting shaft through both a through hole of the outer ring tube and a through hole of the inner ring tube, performing processing of making an end portion of the connecting shaft increase in diameter by plastic working of pushing and stretching the end portion in a radial direction of the connecting shaft; fixing an outer peripheral surface of the connecting shaft to the through hole of the outer ring tube by bringing the outer peripheral surface into close contact with the through hole of the outer ring tube; and rotatably connecting the one of the two adjacent ring tubes to the other one of the two adjacent ring tubes.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, embodiments of an endoscope bending tube manufacturing method and an endoscope, according to the present disclosure, will be described, while reference is made to the drawings. The present disclosure is not limited to the following embodiments, and components in the following embodiments include any component that is easily substitutable by a person skilled in the art, or any component that is substantially the same.

Configuration of Endoscope

Figure 1:
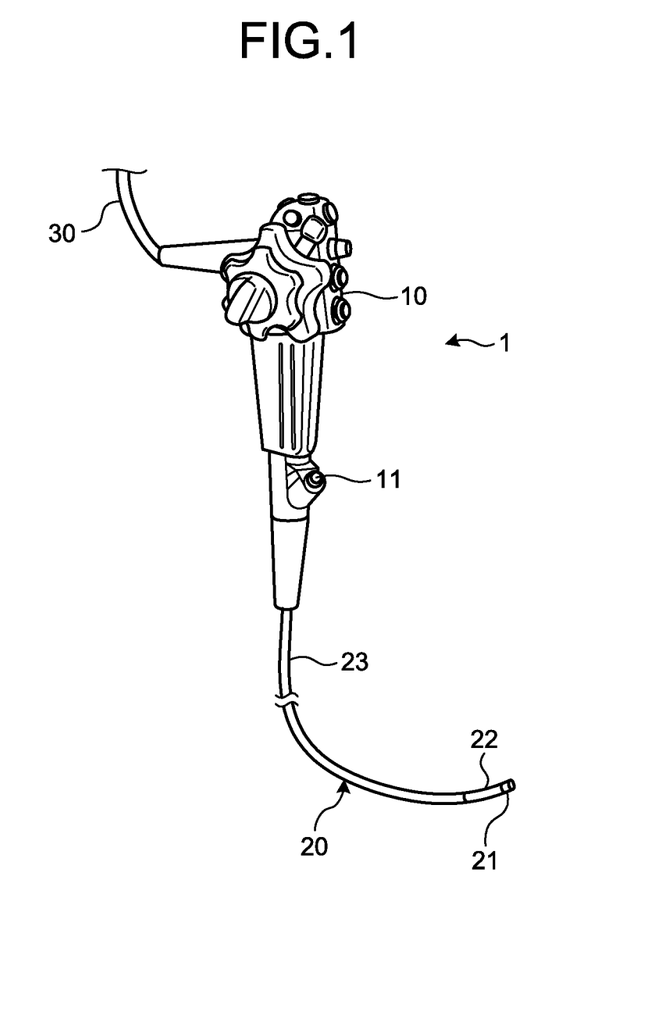
FIG. 1 is a schematic diagram illustrating a configuration of main parts of an endoscope according to an embodiment of the present disclosure.

First of all, a configuration of an endoscope according to an embodiment of the present disclosure will be described while reference is made to FIG. 1. An endoscope 1 includes, as illustrated in FIG. 1, an operating unit 10, an insertion unit 20, and a universal cord 30.

The operating unit 10 is connected at a proximal end of the insertion unit 20; and has various buttons, knobs, and the like provided therein, through which endoscopic functions are operated. The operating unit 10 has a treatment tool insertion opening 11, through which treatment tools, such as biopsy forceps, an electric knife, and an inspecting probe, are inserted into a body cavity of a subject.

The insertion unit 20 is formed of: a distal end portion 21 that is inserted into the body cavity of the subject upon endoscopic examination and has an imaging device (illustration thereof being omitted) provided therein, the imaging device being for capture of in-vivo images of the subject; a bending portion 22 that is connected to a proximal end the distal end portion 21; and a flexible tube portion 23 that is connected to a proximal end of the bending portion 22.

The bending portion 22 is bent by operation of a bending operation knob provided in the operating unit 10, and is bendable in, for example, four directions, upward, downward, leftward, and rightward, in association with pulling and loosening of a bending wire (illustration thereof being omitted) inserted therethrough. Further, the bending portion 22 is specifically formed of: a bending tube 22a (see FIG. 2 described later) that has the bending wire and the like housed therein and is made of metal; and a covering (illustration thereof being omitted) that covers an outer periphery of the bending tube 22a.

Provided inside the universal cord 30 are: a cable and the like connected to the imaging device and the like built in the distal end portion 21; and a light guide for transmitting light from a light source.

Configuration of Endoscope Bending Tube

Figure 2:
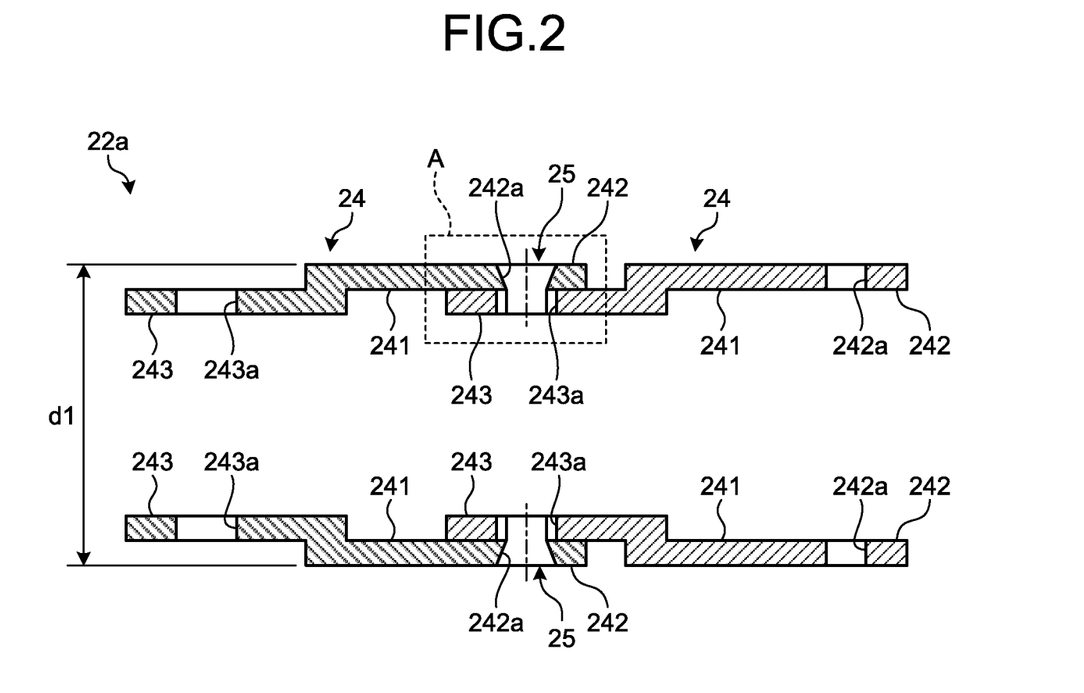
FIG. 2 is a sectional view illustrating a first configuration of an endoscope bending tube according to the embodiment of the present disclosure.
Figure 3:
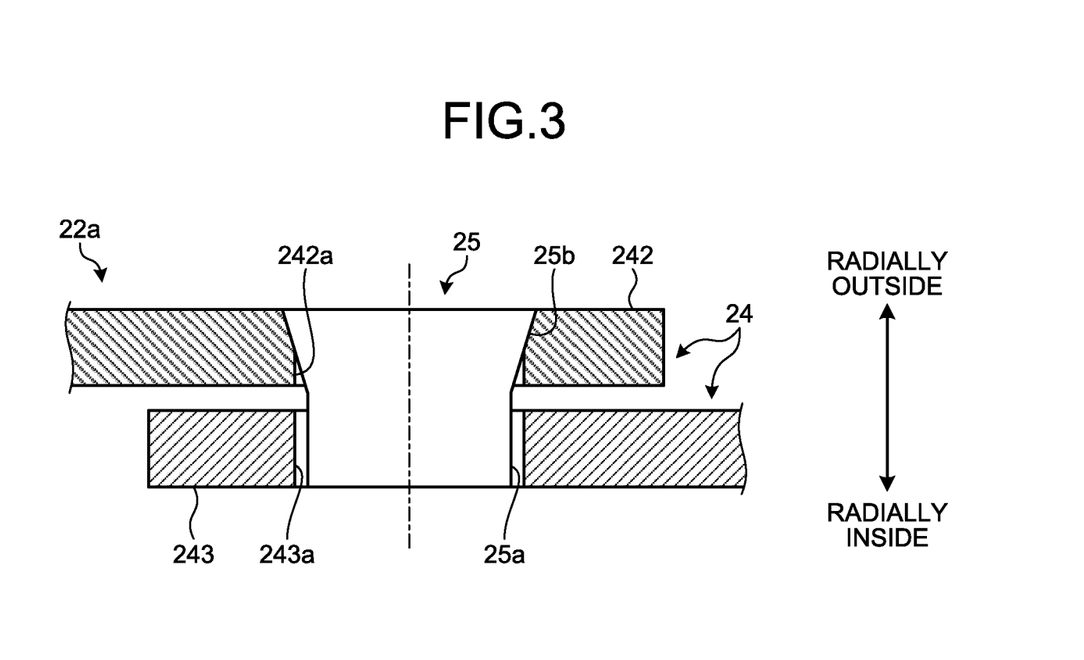
FIG. 3 is a sectional view illustrating the first configuration of the endoscope bending tube according to the embodiment of the present disclosure, the sectional view being an enlarged view of an A-portion in FIG. 2.

Hereinafter, a configuration of an endoscope bending tube according to the embodiment of the present disclosure will be described while reference is made to FIG. 2 and FIG. 3. FIG. 2 is a sectional view illustrating just two adjacent ones of ring tubes 24 from the bending portion 22 illustrated in FIG. 1. Further, FIG. 3 is a sectional view with a configuration of an A-portion in FIG. 2 (see a broken lined portion) having been enlarged.

The bending tube 22a according to the embodiment is, as illustrated in FIG. 2, formed by connection of plural ring tubes 24 in series. Each of the ring tubes 24 includes: a ring tube body 241 that is cylindrical; a pair of tongue pieces 242 provided at one end of the ring tube body 241, the tongue pieces 242 facing each other; a pair of tongue pieces 243 provided at the other end of the ring tube body 241, the tongue pieces 243 facing each other; and connecting shafts 25 that rotatably connect the two adjacent ring tubes 24.

The tongue pieces 242 are provided, as illustrated in FIG. 2, to protrude in an axial direction of the ring tube 24 at the one end of the ring tube body 241. Further, the tongue pieces 242 each have a through hole 242a formed therein, in a through-thickness direction (a radial direction of the ring tube 24).

The tongue pieces 243 are provided, as illustrated in FIG. 2, to protrude in the axial direction of the ring tube 24 at the other end of the ring tube body 241, and are provided more inward in a radial direction of the bending tube 22a than the tongue pieces 242. As illustrated in FIG. 3, a predetermined gap is provided between an inner peripheral surface of the tongue piece 242 and an outer peripheral surface of the tongue piece 243, such that the ring tubes 24 move rotatably. Further, the tongue pieces 243 each have a through hole 243a formed therein, the through hole 243a providing a predetermined fitting gap from the connecting shaft 25 such that the ring tubes 24 move rotatably.

The two adjacent ring tubes 24 are, as illustrated in FIG. 2 and FIG. 3, arranged in a state where the tongue pieces 242 and the tongue pieces 243 are overlapped with each other, such that positions of the through holes 242a and positions of the through holes 243a match each other along the axial direction of the ring tubes 24. That is, the through holes 242a of one of the two adjacent ring tubes 24 and the through holes 243a of the other one of the two adjacent ring tubes 24 are positioned such that their centers respectively match each other.

The connecting shafts 25 are, as illustrated in FIG. 2, each inserted through both the through hole 242a of the ring tube 24 arranged at a radially outer side of the bending tube 22a and the through hole 243a of the ring tube 24 arranged at a radially inner side of the bending tube 22a. The connecting shafts 25 are each formed such that a part thereof has increasing diameter. That is, each of the connecting shafts 25 has, as illustrated in FIG. 3, a columnar portion 25a having a cross-sectional area that is constant along a shaft direction thereof, and a diameter increasing portion 25b that increases in diameter outward in the radial direction of the bending tube 22a.

As illustrated in FIG. 3, at least a part of the diameter increasing portion 25b is in close contact with the through hole 242a, and the diameter increasing portion 25b is thus fixed to the through hole 242a. However, the columnar portion 25a is not fixed to the through hole 243a. That is, the connecting shaft 25 is fixed to the ring tube 24 that is arranged at the radially outer side of the bending tube 22a (the side where the through hole 242a is formed), but is not fixed to the ring tube 24 arranged at the radially inner side of the bending tube 22a (the side where the through hole 243a is formed). Thereby, one of the two adjacent ring tubes 24 in the bending tube 22a is rotatably connected to the other one thereof, via the connecting shaft 25.

The bending tube 22a has, as illustrated in FIG. 3, a paired structure, and an amount of protrusion of the connecting shaft 25 fixed to the tongue piece 242 is larger than a gap between the tongue piece 242 and the tongue piece 243 that have been combined together. Therefore, the two adjacent ring tubes 24 will not fall off from each other.

In the bending tube 22a configured as described above, since the connecting shafts 25 will not protrude radially outward from the bending tube 22a, an outer diameter d1 of the bending tube 22a is smaller than the conventional outer diameter d2 (see FIG. 7). Further, since the connecting shafts 25 will not protrude radially inward from the bending tube 22a, even if the inner diameter of the bending tube 22a is decreased, interference with a built-in element housed in the bending tube 22a does not occur. Accordingly, the diameter of the bending tube 22a is able to be reduced, and burdens on patients upon endoscopic examination are able to be reduced.

The conventional bending tube 122a has a problem that the connecting shaft 125 protruding radially outward interferes with a covering (illustration thereof being omitted) of the bending tube 122a and the covering thus tends to be damaged. In contrast, the bending tube 22a according to the embodiment does not have this problem, since the connecting shaft 25 does not interfere with the covering.

Endoscope Bending Tube Manufacturing Method

Hereinafter, an endoscope bending tube manufacturing method according to the embodiment of the present disclosure will be described while reference is made to FIG. 4A to FIG. 6. The manufacturing method for the bending tube 22a according to the embodiment includes a ring tube arranging process and a ring tube connecting process.

Firstly, in the ring tube arranging process, one of the two adjacent ring tubes 24 and an other one of the two adjacent ring tubes 24 are arranged to match positions of the pair of the through holes 242a formed at one end of the one of the two adjacent ring tubes 24 with positions of the pair of the through holes 243a formed at one end of the other one of the two adjacent ring tubes 24. That is, in this process, the two adjacent ring tubes 24 are arranged in a state where the tongue pieces 242 are overlapped with the tongue pieces 243, such that the positions of the through holes 242a and the positions of the through holes 243a match each other along the axial direction of the ring tubes 24.

Figure 4A:
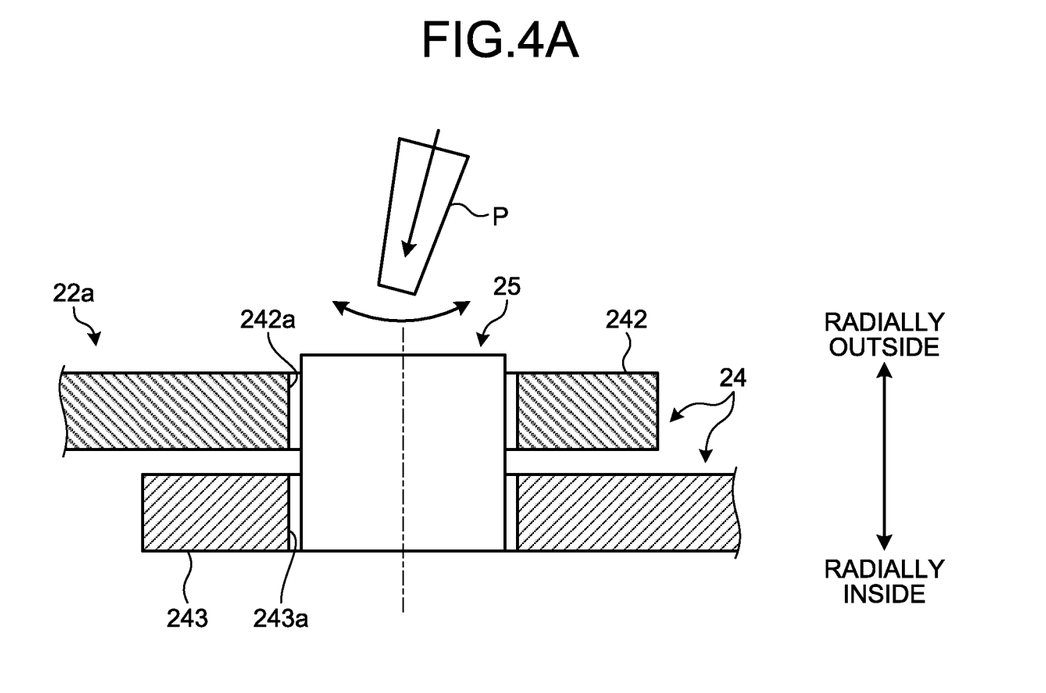
FIG. 4A is a sectional view illustrating a manufacturing method for the first configuration of the endoscope bending tube according to the embodiment of the present disclosure.

Subsequently, in the ring tube connecting process, the connecting shaft 25 is inserted through both the through hole 242a of the ring tube 24 arranged at the radially outer side of the bending tube 22a and the through hole 243a of the ring tube 24 arranged at the radially inner side of the bending tube 22a. The connecting shaft 25 is, as illustrated in FIG. 4A, formed in a columnar shape having a cross-sectional area that is constant throughout the connecting shaft 25 along its shaft direction. Further, in this process, the connecting shaft 25 is arranged so as to protrude slightly outward from an outer peripheral surface of the ring tube 24 arranged at the radially outer side of the bending tube 22a.

Figure 4B:
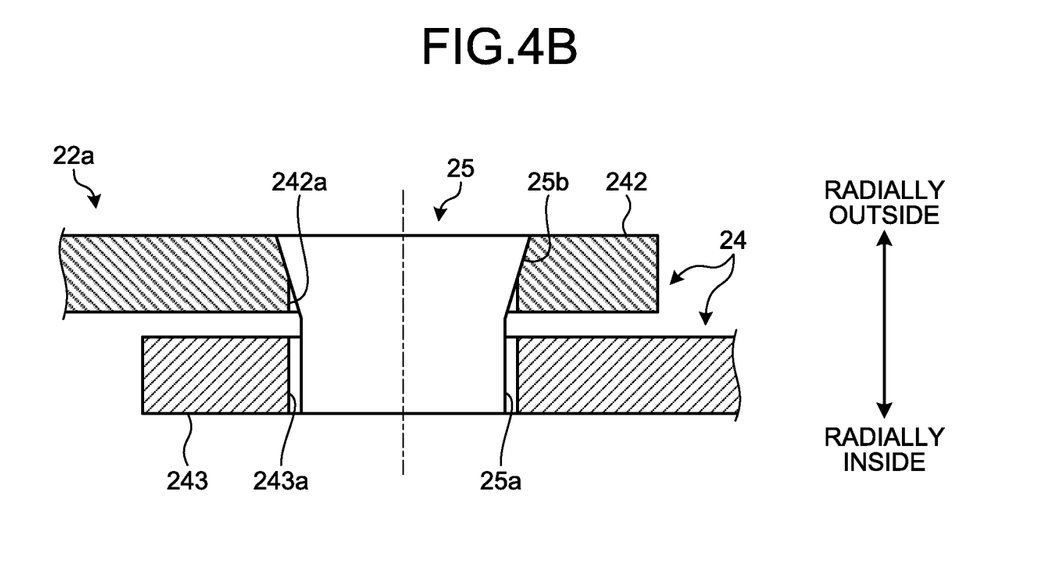
FIG. 4B is a sectional view illustrating the manufacturing method for the first configuration of the endoscope bending tube according to the embodiment of the present disclosure.

Subsequently, processing where an end portion (a portion inserted in the through hole 242a) of the connecting shaft 25 is made to increase in diameter outward in the radial direction of the bending tube 22a is performed. Specifically, as illustrated in FIG. 4A, by radial caulking (precision caulking), plastic working is performed such that the end portion of the connecting shaft 25 is pushed and stretched in the radial direction by a punch P. Thereby, as illustrated in FIG. 4B, the end portion of the connecting shaft 25 has increasing diameter, and an outer peripheral surface of the connecting shaft 25, that is, a part of the diameter increasing portion 25b, is thus fixed to the through hole 242a. One of the two adjacent ring tubes 24 is thus rotatably connected to the other one thereof.

In the ring tube connecting process, by the above described plastic working, the end portion of the connecting shaft 25 is squashed toward the through hole 242a, the end portion having protruded from the outer peripheral surface of the ring tube 24, and as illustrated in FIG. 4B, the end portion of the connecting shaft 25 is thus made to be positioned to a height that is substantially the same as that of the outer peripheral surface of the ring tube 24. In the bending tube 22a manufactured by the above described manufacturing method, the connecting shaft 25 will not protrude outside the bending tube 22a, and thus the diameter of the bending tube 22a is able to be reduced.

In the above described ring tube connecting process, the outer peripheral surface of the connecting shaft 25 is fixed to the through hole 242a by the close contact therebetween by use of radial caulking, but the fixing method by close contact is not limited to this method.

Figure 5:
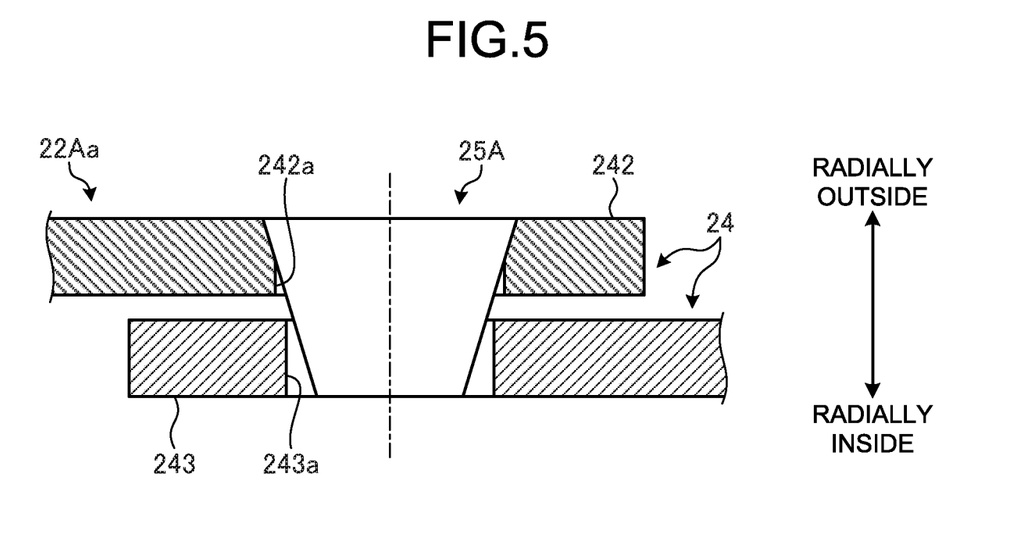
FIG. 5 is a sectional view illustrating a second configuration of the endoscope bending tube according to the embodiment of the present disclosure.

In the ring tube connecting process, for example, as illustrated in FIG. 5, by insertion (press fitting) of a wedge-shaped connecting shaft 25A from a radially outer side of a bending tube 22Aa through both the through hole 242a and the through hole 243a, an outer peripheral surface of the connecting shaft 25A may be brought into close contact with the through hole 242a to be fixed thereto. This method enables manufacture of the bending tube 22Aa by connection of the adjacent ring tubes 24 in an even simpler way, without use of caulking as described above.

Figure 6:
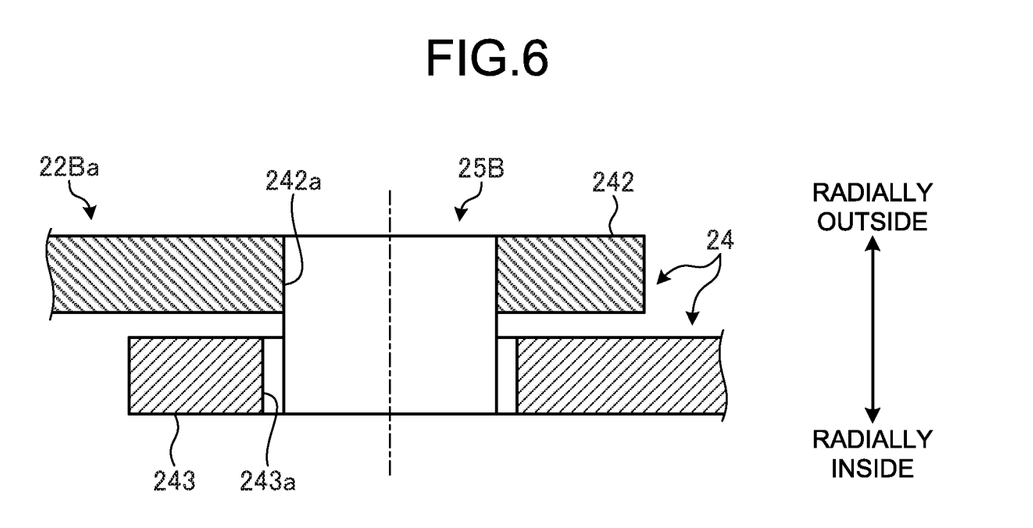
FIG. 6 is a sectional view illustrating a third configuration of the endoscope bending tube according to the embodiment of the present disclosure.

Further, in the ring tube connecting process, for example, as illustrated in FIG. 6, two adjacent ones of the ring tubes 24 may be connected by use of a columnar connecting shaft 25B. In this case, an outer peripheral surface of the connecting shaft 25B may be brought into close contact with the through hole 242a to be fixed thereto by, for example, bonding of the connecting shaft 25B to the through hole 242a. Or, the outer peripheral surface of the connecting shaft 25B may be brought into close contact with the through hole 242a to be fixed thereto, by press fitting of the connecting shaft 25B, which has a diameter larger than that of the through hole 242a, into the through hole 242a. These methods enable manufacture of a bending tube 22Ba by connection of adjacent ones of the ring tubes 24 in an even simpler way, without use of caulking as described above.

Hereinbefore, the endoscope bending tube manufacturing method and the endoscope, according to the present disclosure, have been specifically described through modes for carrying out the disclosure, but the gist of the present disclosure is not limited to the description thereof, and should be broadly interpreted based on description in the claims. Further, needless to say, various modifications based on the description are also included in the gist of the present disclosure.

For example, in FIG. 3, FIG. 5, and FIG. 6, each of end portions of the connecting shafts 25, 25A, and 25B is provided up to a position that is the same as that of the inner peripheral surface of the bending tube 22a, 22Aa, or 22Ba (the inner peripheral surface of the tongue piece 243); but the connecting shafts 25, 25A, and 25B may be shortened such that each of the end portions of the connecting shafts 25, 25A, and 25B is positioned in the through hole 243a, as long as the ring tubes 24 are able to be prevented from falling off.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope bending tube manufacturing method of manufacturing a bending tube of an endoscope, by connecting plural ring tubes forming the bending tube, the endoscope bending tube manufacturing method comprising:
   arranging one of two adjacent ring tubes on an outer side of the other of the two adjacent ring tubes to match positions of a pair of through holes formed at one end of the one that is an outer ring tube,
   with positions of a pair of through holes formed at one end of the other one that is an inner ring tube, the through holes of the outer ring tube being formed in a radial direction of the outer ring tube, and the through holes of the inner ring tube being formed in a radial direction of the inner ring tube;
   inserting a connecting shaft through both a through hole of the outer ring tube and a through hole of the inner ring tube such that a first end portion of the connecting shaft from is flush with an inner peripheral surface of the inner ring tube and does not protrude past the inner peripheral surface of the inner ring tube; and
   performing plastic working of pushing and stretching a second end portion of the connecting shaft in a radial direction of the connecting shaft to enlarge an outer diameter of the second end portion,
   the second end portion being an end portion of the connecting shaft on an outer side of the outer ring tube, and the enlargement of the outer diameter of the second end portion causing an inner diameter of the through hole of the outer ring tube to enlarge as a result of a close contact between an outer peripheral surface of the connecting shaft and an inner peripheral surface of the through hole of the outer ring tube, so that the outer peripheral surface of the connecting shaft and the inner peripheral surface of the through hole of the outer ring tube are fixed to each other in close contact, thereby connecting the two adjacent ring tubes to each other in such a way that the two adjacent ring tubes are rotatable relative to each other.

2. The endoscope bending tube manufacturing method according to claim 1, wherein the plastic working comprises plastic working that is performed by radial caulking.

* * * * *